United States Patent
Madapati

(10) Patent No.: US 9,810,537 B2
(45) Date of Patent: Nov. 7, 2017

(54) METHOD OF PREVIEWING OFF-ROAD TRAILS AND VIEWING ASSOCIATED HEALTH REQUIREMENTS AND RELATED SYSTEM

(71) Applicant: MITAC INTERNATIONAL CORP., Taoyuan (TW)

(72) Inventor: Naveen Madapati, Santa Clara, CA (US)

(73) Assignee: MITAC INTERNATIONAL CORP., Taoyuan (TW)

( * ) Notice: Subject to any disclaimer, the term of this patent is extended or adjusted under 35 U.S.C. 154(b) by 15 days.

(21) Appl. No.: 15/073,636

(22) Filed: Mar. 17, 2016

(65) Prior Publication Data

US 2017/0268884 A1    Sep. 21, 2017

(51) Int. Cl.
*G01C 21/00* (2006.01)
*G01C 21/20* (2006.01)
*A61B 5/00* (2006.01)
*A61B 5/11* (2006.01)

(52) U.S. Cl.
CPC ............ *G01C 21/20* (2013.01); *A61B 5/0022* (2013.01); *A61B 5/0024* (2013.01); *A61B 5/1112* (2013.01); *A61B 5/486* (2013.01); *A61B 5/6898* (2013.01)

(58) Field of Classification Search
CPC ...... G01C 21/20; G01C 21/34; A61B 5/0022; A61B 5/0024; A61B 5/1112; A61B 5/486; A61B 5/6898; G06F 3/04842
USPC .......................... 701/36, 418, 409, 424, 431
See application file for complete search history.

(56) References Cited

U.S. PATENT DOCUMENTS

| | | | |
|---|---|---|---|
| 6,356,837 B1 * | 3/2002 | Yokota | G01C 21/34 701/411 |
| 7,003,397 B2 * | 2/2006 | Yokota | G01C 21/26 340/990 |
| 7,933,395 B1 | 4/2011 | Bailly | |
| 8,090,532 B2 | 1/2012 | Tashev | |
| 8,700,331 B2 | 4/2014 | Moore | |
| 9,047,691 B2 | 6/2015 | van Os | |
| 9,080,883 B2 | 7/2015 | Frey | |
| 9,103,688 B2 | 8/2015 | Pivonka | |
| 9,157,759 B2 | 10/2015 | Lukassen | |
| 9,202,111 B2 * | 12/2015 | Arnold | G06Q 30/0207 |
| 2012/0116550 A1 * | 5/2012 | Hoffman | G06F 17/30772 700/91 |
| 2014/0244110 A1 * | 8/2014 | Tharaldson | G07C 5/008 701/36 |
| 2014/0288680 A1 * | 9/2014 | Hoffman | G06K 9/00342 700/91 |

FOREIGN PATENT DOCUMENTS

TW    I346770 B    8/2011

* cited by examiner

*Primary Examiner* — Gertrude Arthur Jeanglaude
(74) *Attorney, Agent, or Firm* — Winston Hsu

(57) ABSTRACT

A method of previewing off-road trails and viewing associated health requirements includes receiving selection of an off-road trail from a user, and displaying an overview of the selected off-road trail in response to receiving selection of the selected off-road trail from the user, the overview of the selected off-road trail indicating latitude and longitude coordinates associated with the selected off-road trail, elevation data associated with the selected off-road trail, and recommended minimum health guidelines associated with the selected off-road trail.

20 Claims, 6 Drawing Sheets

METHOD OF PREVIEWING OFF-ROAD TRAILS AND VIEWING ASSOCIATED HEALTH REQUIREMENTS AND RELATED SYSTEM

BACKGROUND OF THE INVENTION

1. Field of the Invention

The invention relates to a navigation device, and more particularly, to a navigation device that allows a user to preview health requirements associated with off-road trails.

2. Description of the Prior Art

Global Positioning System (GPS) based navigation devices are well known and are widely employed as in-car navigation devices. Common functions of a navigation device include providing a map database for generating navigation instructions that are then shown on a display of the navigation device. These navigation devices are often mounted on or in the dashboard of a vehicle using a suction mount or other mounting means.

The term "navigation device" refers to a device that enables a user to navigate to a pre-defined destination. The device may have an internal system for receiving location data, such as a GPS receiver, or may merely be connectable to a receiver that can receive location data. The device may compute a route itself, or communicate with a remote server that computes the route and provides navigation information to the device, or a hybrid device in which the device itself and a remote server both play a role in the route computation process. Portable GPS navigation devices are not permanently integrated into a vehicle but instead are devices that can readily be mounted in or otherwise used inside a vehicle. Generally (but not necessarily), they are fully self-contained—i.e. include an internal GPS antenna, navigation software and maps and can hence plot and display a route to be taken. The navigation devices can either be personal navigation devices such as GPS devices or mobile phones that contain the functionality of GPS receivers and navigation software.

When a user of a navigation device decides to go on a selected off-road trail, the user relies heavily on static data associated with the selected off-road trail that is often provided on a website. The user will usually only be provided with information about the trail condition, and the user will not be provided with any minimum health guidelines associated with traveling on the selected off-road trail. Furthermore, if the user were to attempt the selected off-road trail and then get stuck partway through the selected off-road trail, the user would not have a good indication of what would be required to complete the remaining part of the selected off-road trail. What's more, the user's health condition is a dynamic value, and can change as the user travels on the selected off-road trail. Current navigation devices do not give the user customized suggestions depending on the user's real-time fitness data.

SUMMARY OF THE INVENTION

It is therefore one of the primary objectives of the claimed invention to provide a method of previewing off-road trails and viewing associated health requirements.

According to an exemplary embodiment of the claimed invention, a method of previewing off-road trails and viewing associated health requirements is disclosed. The method includes receiving selection of an off-road trail from a user, and displaying an overview of the selected off-road trail in response to receiving selection of the selected off-road trail from the user, the overview of the selected off-road trail indicating latitude and longitude coordinates associated with the selected off-road trail, elevation data associated with the selected off-road trail, and recommended minimum health guidelines associated with the selected off-road trail.

According to another exemplary embodiment of the claimed invention, a system for previewing off-road trails and viewing associated health requirements is disclosed. The system includes a navigation device, comprising a user interface receiving selection of an off-road trail from a user, and displaying an overview of the selected off-road trail in response to receiving selection of the selected off-road trail from the user, the overview of the selected off-road trail indicating latitude and longitude coordinates associated with the selected off-road trail, elevation data associated with the selected off-road trail, and recommended minimum health guidelines associated with the selected off-road trail.

It is an advantage that the present invention supplies the user with recommended minimum health guidelines associated with a selected off-road trail so that the user can adequately gauge whether the user is capable of traveling on the selected off-road trail. In addition, the user is given the opportunity to see an overview of the selected off-road trail so that the user can easily and conveniently find out more details about the selected off-road trail, including the recommended minimum health guidelines.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
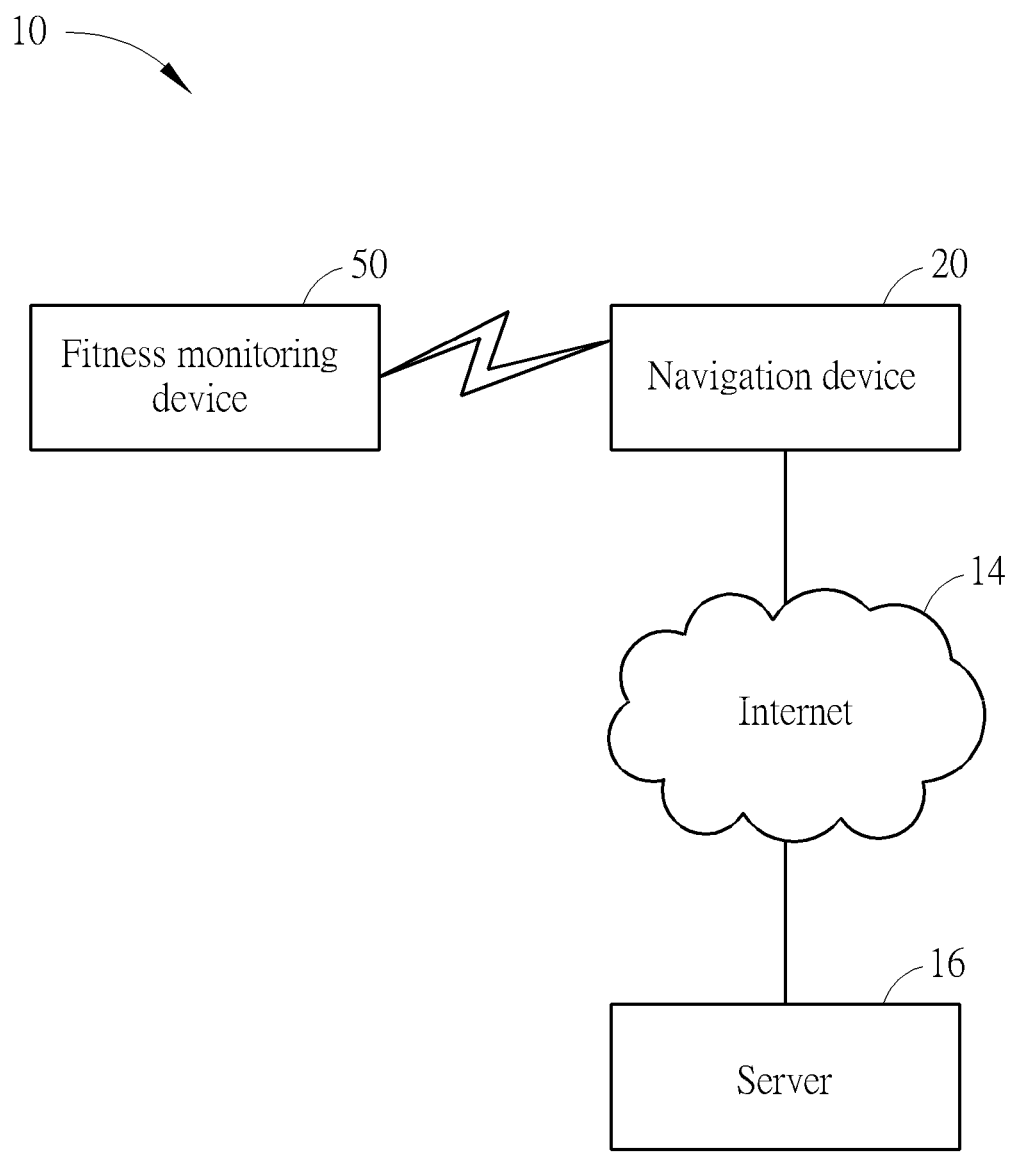
FIG. 1 is a block diagram of a system for previewing off-road trails and viewing associated health requirements according to the present invention.

Please refer to FIG. 1. FIG. 1 is a block diagram of a system 10 for previewing off-road trails and viewing associated health requirements according to the present invention. The system 10 comprises a fitness monitoring device 50. The fitness monitoring device 50 can be worn by the user in order to sense real-time fitness data produced by the user. The fitness monitoring device 50 may be a fitness band or any other type of device that is worn by the user for sensing real-time fitness data.

The system 10 further comprises a navigation device 20 for guiding a user to destinations by providing navigation instructions to the destinations. The navigation device 20 is able to receive cloud data from a server 16 through the internet 14. The cloud data stored in the server 16 includes stored trail data including overviews of off-road trails stored in a database. The server 16 may also optionally store historical fitness data corresponding to individual users. The navigation device 20 may be a personal navigation device, also called a "GPS device", or a mobile phone.

Figure 2:
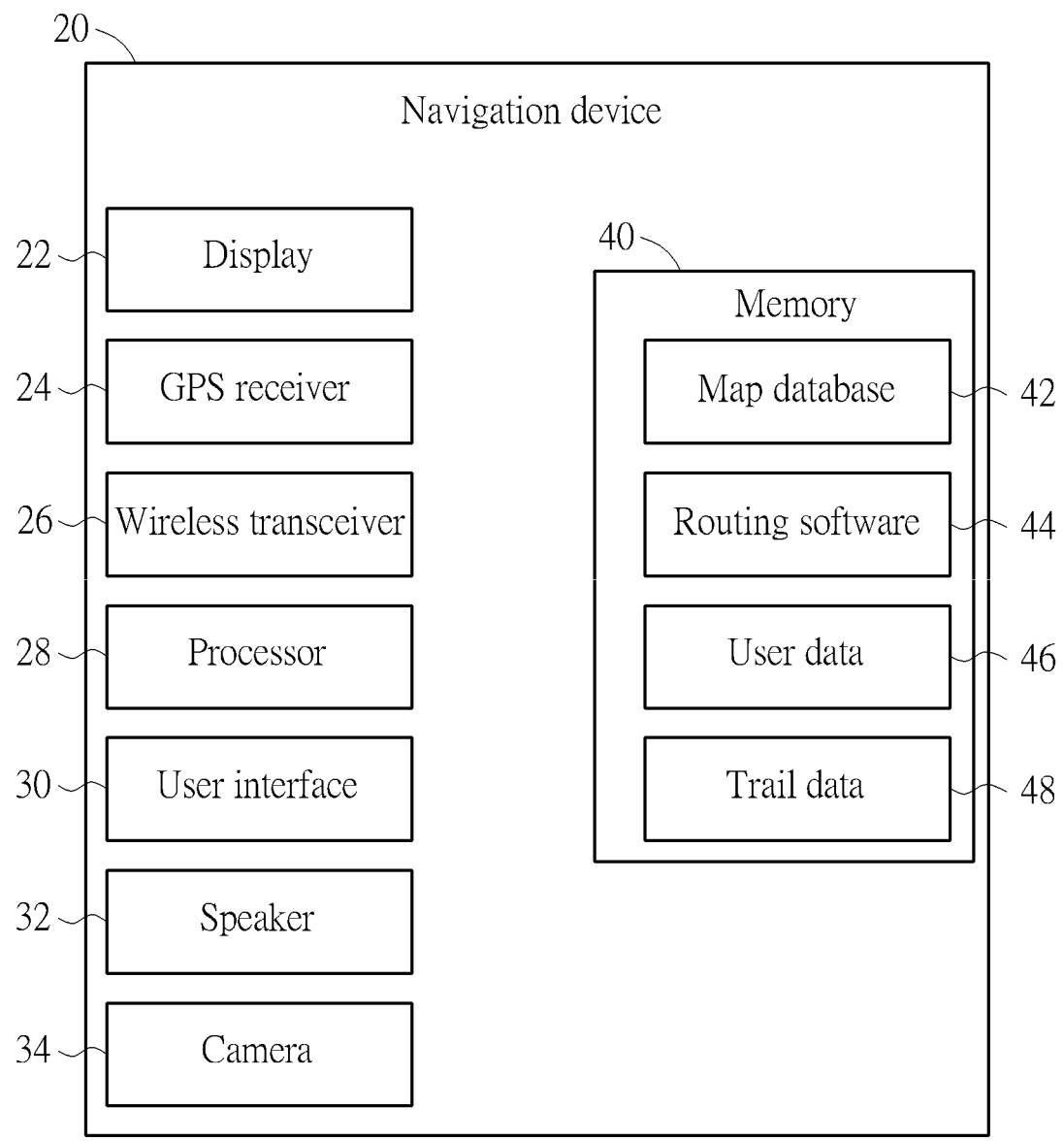
FIG. 2 is a functional block diagram of the navigation device according to the present invention.

Please refer to FIG. 2. FIG. 2 is a functional block diagram of the navigation device 20 according to the present invention. The navigation device 20 contains a display 22 which can be a touch sensitive display, a GPS receiver 24 for receiving the current coordinates of the navigation device 20, and a wireless transceiver 26 such as a Wireless Fidelity (Wi-Fi) transceiver or Bluetooth transceiver, or a mobile internet transceiver such as a third generation of mobile telecommunications technology (3G) transceiver or a fourth generation of mobile telecommunications technology (4G) transceiver for allowing the navigation device 20 to receive cloud data from the server 16 via the internet 14. The navigation device 20 also comprises a processor 28 for controlling operation of the navigation device 20 and executing code for operating the navigation device 20, a user interface 30, a speaker 32, a camera 34 capable of capturing still photos and video, and memory 40. The memory 40 may be non-volatile memory such as flash memory, and is used to store a map database 42 containing map data and points of interest. The memory 40 also stores routing software 44, any user data 46 that the user wishes to store, and trail data 48 containing information about off-road trails stored in the memory 40. The user data 46 may optionally store the user's historical fitness data, may store other preferences the user may have, and may store information related to which off-road trails the user has been on in the past. The routing software 44 is executed by the processor 28, and provides navigational guidance to destinations.

Figure 3:
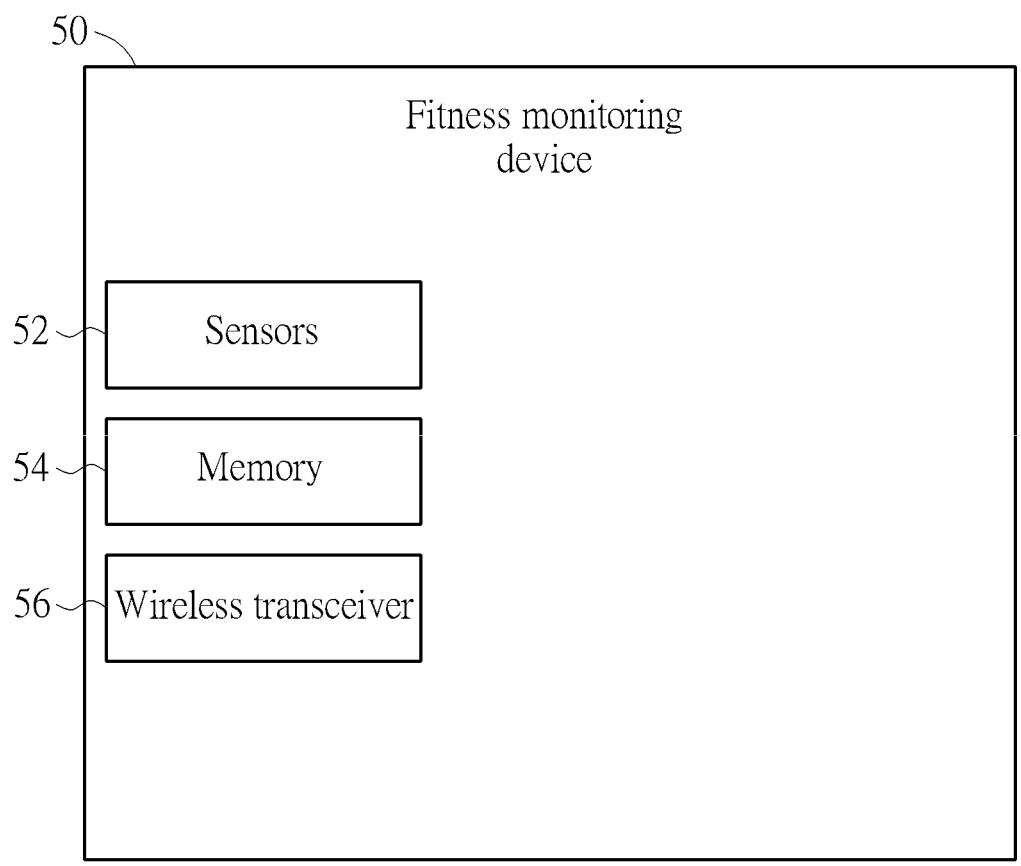
FIG. 3 is a functional block diagram of the fitness monitoring device according to the present invention.

Please refer to FIG. 3. FIG. 3 is a functional block diagram of the fitness monitoring device 50 according to the present invention. The fitness monitoring device 50 contains one or more sensors 52 for sensing real-time fitness data associated with the user of the fitness monitoring device 50. In a preferred embodiment, multiple sensors 52 are used for sensing a variety of different types of real-time fitness data, but the present invention can use only one sensor as well. These sensors 52 may include an accelerometer, an electrochemical sensor, a heart rate monitor, a blood pressure monitor, a blood oxygen saturation monitor, a body temperature sensor, an electrocardiogram (ECG) sensor, and so on. The fitness monitoring device 50 also contains a memory 54 for storing the real-time fitness data as it is produced, and the memory may also optionally store the user's historical fitness data. The fitness monitoring device 50 also includes a wireless transceiver 56 such as a Wi-Fi transceiver or Bluetooth transceiver, and this wireless transceiver 56 may communicate with the wireless transceiver 26 of the navigation device 20 for sending real-time fitness data as well as historical fitness data from the fitness monitoring device 50 to the navigation device 20.

The present invention makes uses of the user's fitness data when the user is either trying to select which off-road trail to go on, or when the user is already traveling on a selected off-road trail. Please note that "traveling" on the selected off-road trail can refer to hiking or walking on the selected off-road trail or driving a vehicle on the selected off-road trail. In either instance, the user's fitness data may affect how the user is able to cope with the selected off-road trail.

Figure 4:
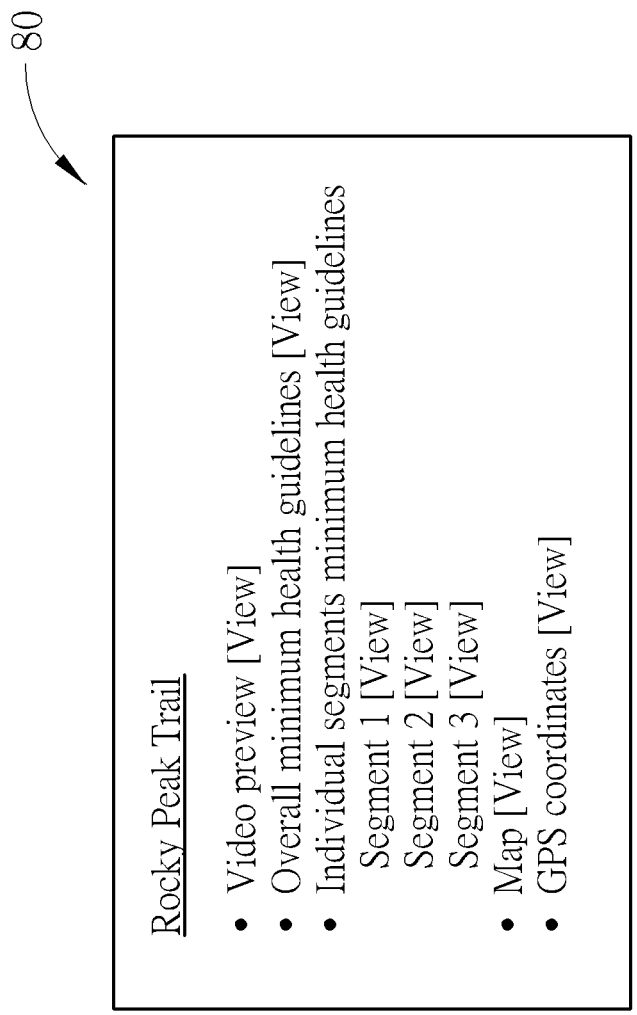
FIG. 4 illustrates an example of an overview given for a selected off-road trail.

Please refer to FIG. 4. FIG. 4 illustrates an example of an overview 80 given for a selected off-road trail. The overview 80 shown in FIG. 4 corresponds to the selected off-road trail named the "Rocky Peak Trail". The overview 80 contains a variety of different types of details about the selected off-road trail. In FIG. 4 each of the different details is shown as being available when clicking on or tapping on a hyperlink labeled "[View]". Of course, these details can also be shown in other forms with or without the need to first follow a hyperlink.

The overview 80 can be viewed on a computing device such as a computer or a mobile phone that is able to connect to the server 16 via the internet 14 for viewing cloud data, or the overview 80 may be stored locally in the trail data 48 portion of the memory 40 of the navigation device 20 for viewing on the display 22 of the navigation device 20. The overview 80 shown in FIG. 4 allows the user to see a video preview of the selected off-road trail. The video preview is captured using a video camera as someone travels over the selected off-road trail. If the selected off-road trail already has a video preview available, the user is able to see the video preview at his or her leisure. The user can see the video preview before setting off for the selected off-road trail, or the user can even see the video preview while the user is already traveling on the selected off-road trail. In this way, if the user gets stuck on or feels unsure about continuing on the selected off-road trail, the user can see the video preview while the user is already traveling on the selected off-road trail in order to help the user decide whether or not to continue on the selected off-road trail.

The overview 80 may also provide information on overall recommended minimum health guidelines for the entire selected off-road trail. These health guidelines can indicate what kind of fitness statistics the user is recommended to have in order for the user to attempt the selected off-road trail. The overall recommended minimum health guidelines for the entire selected off-road trail will indicate the strictest requirements needed to complete the entire selected off-road trail. For instance, a recommended blood pressure, resting heart rate, and age level can be given, along with certain health conditions that are not recommended for the selected off-road trail. The user is also given the opportunity to see recommended minimum health guidelines for individual segments of the selected off-road trail. This can break the selected off-road trail down into individual segments, such as the three segments that are shown in the overview 80 in FIG. 4. Certain segments may be more challenging than others, so the user may be able to attempt certain less challenging segments of the selected off-road trail without traveling on the entire selected off-road trail. The user may also wish to view a map of the selected off-road trail, and different types of maps may be given such as a street map, a terrain map, relief map, and so on. GPS coordinates and elevations of different parts of the selected off-road trail can also be shown to the user in the overview 80. While the user is viewing any of the details in the overview 80, other pertinent information can also be shown at the same time. For example, while watching the video preview of the selected off-road trail, the user can also be shown latitude and longitude coordinates associated with segments of the selected off-road trail, elevation data associated with segments of the selected off-road trail, and recommended minimum health guidelines associated with segments of the selected off-road trail while the video preview is playing.

If no overview is available for a selected off-road trail, the user can be given the chance to create an overview when the user travels on the selected off-road trail. Instead of a single overview, multiple overview versions can also be stored in the server 16 so users can have the chance to see different users' perspectives of the selected off-road trail. When the user is creating or updating an overview of a selected off-road trail, the following items are recorded as the user travels on the selected off-road trail. The fitness monitoring device 50 records real-time fitness data for the user, the camera 34 of the navigation device 20 records video, and the GPS receiver 24 of the navigation device 20 records latitude and longitude coordinates and elevation data as the user travels on the selected off-road trail. Then the navigation device 20 synchronizes the real-time fitness data, the recorded video, and the recorded latitude and longitude coordinates and elevation data generated as a result of the user traveling on the selected off-road trail to produce synchronized trail data that will constitute the newly created overview of the selected off-road trail, which can then be saved in the server 16. Please note that more than one camera 34 can record video simultaneously, and multiple cameras can even record a 360-degree view of the selected off-road trail as the user travels on it. By synchronizing the real-time fitness data, the recorded video, and the recorded latitude and longitude coordinates and elevation data, the overview can indicate the difficulty and the health requirements associated with any portion of the selected off-road trail, which provides users with detailed information about which portions of the selected off-road trail may be more or less difficult than others.

When a user is traveling on off-road trails, the user's health condition and the current trail condition of the off-road trails will have a major impact on the user's driving habits and the route that the user ends up taking. Sometimes the user's health condition can vary unexpectedly due to tough trail conditions. In this situation, it is helpful if the navigation device 20 suggests an alternate route for the user to follow instead of the selected off-road trail. When determining that the user's real-time fitness data indicates that the user is not qualified to travel on the selected off-road trail, an easier alternate route can be generated for the user to follow. The user's real-time fitness data can be constantly monitored to determine if the user is still able to continue on the selected off-road trail, and if not, an alternate route is suggested. The user can also even be warned if the user is going too fast when the user's current speed is not recommended for the user's health condition.

Figure 5A:
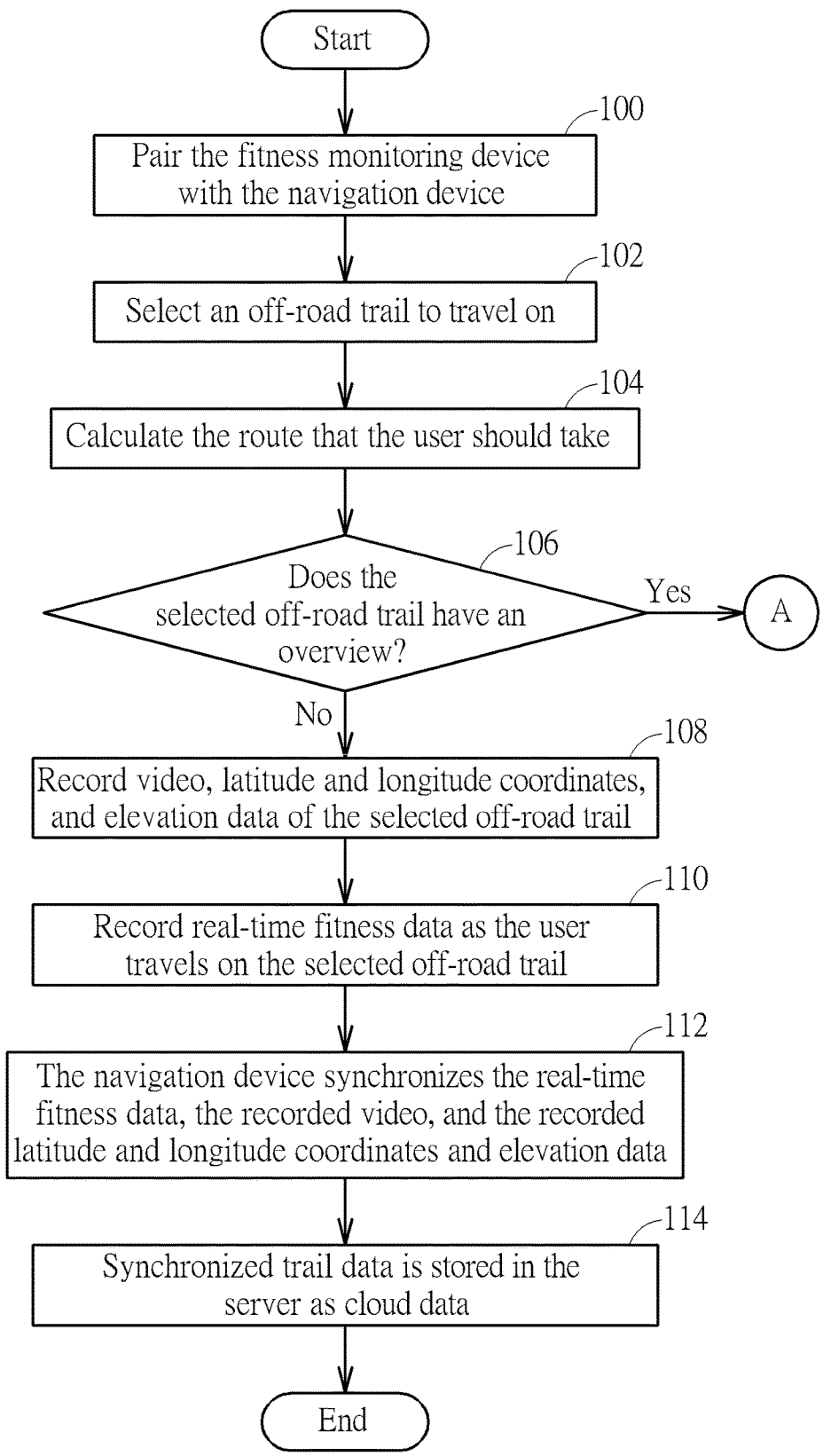
FIG. 5A and FIG. 5B contain a flowchart illustrating a method of creating and previewing off-road trails and associated health requirements, and monitoring health conditions while traveling on a selected off-road trail according to the present invention.
Figure 5B:
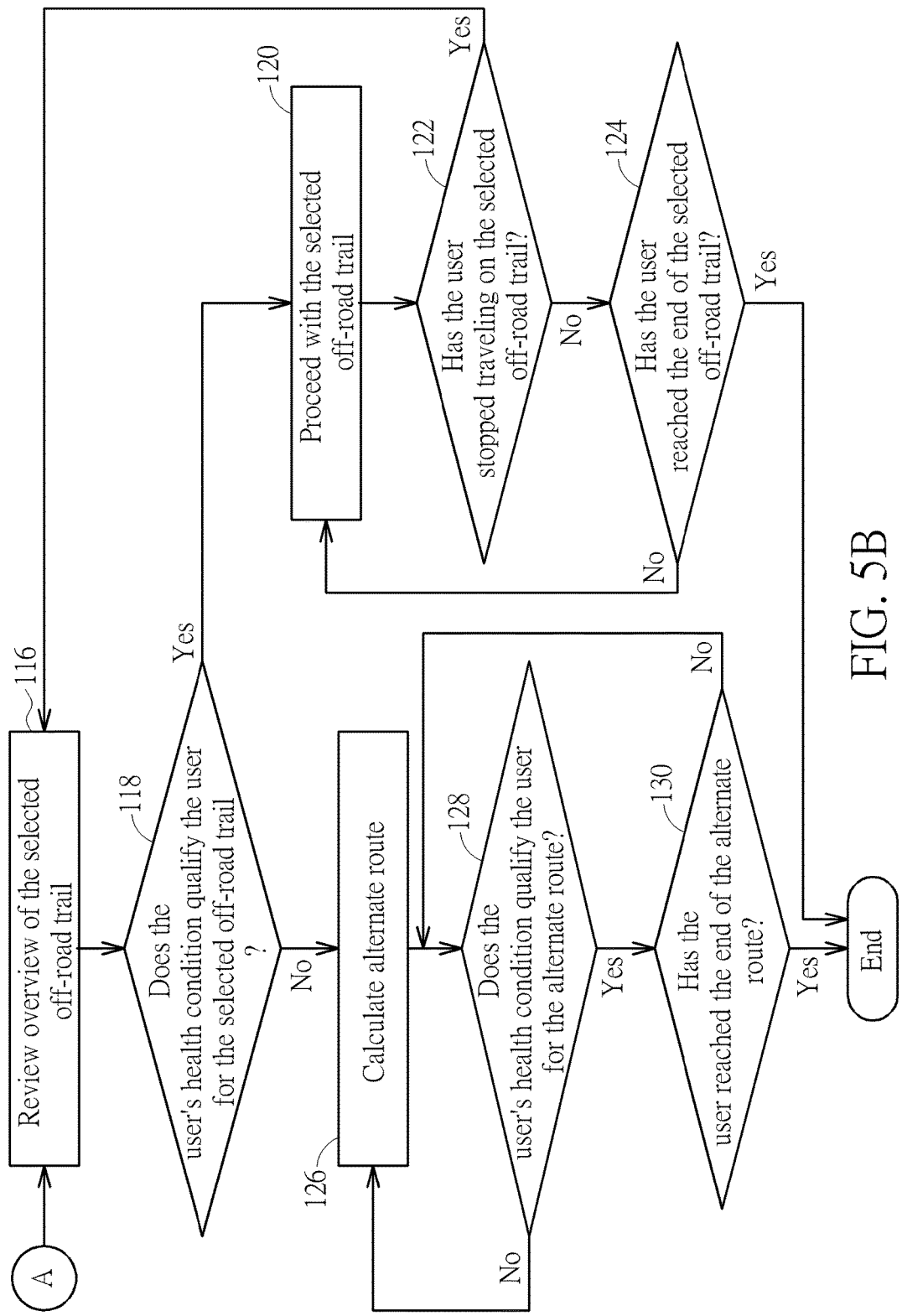

Please refer to FIG. 5A and FIG. 5B. FIG. 5A and FIG. 5B contain a flowchart illustrating a method of creating and previewing off-road trails and associated health requirements, and monitoring health conditions while traveling on a selected off-road trail according to the present invention. Steps contained in the flowchart will be explained below.

Step 100: The user pairs the fitness monitoring device 50 with the navigation device 20.

Step 102: The user selects an off-road trail to travel on. The user can travel on the selected off-road trail by foot or in a vehicle.

Step 104: The routing software 44 of the navigation device 20 calculates the route that the user should take to arrive at and to travel on the selected off-road trail.

Step 106: Determine if the selected off-road trail has an overview providing a video preview and an indication of recommended minimum health guidelines for the selected off-road trail. If the selected off-road trail has an associated overview available, go to step 116. If not, go to step 108.

Step 108: The camera 34 of the navigation device 20 records video of the selected off-road trail, and the GPS receiver 24 of the navigation device 20 records latitude and longitude coordinates and elevation data as the user travels on the selected off-road trail.

Step 110: The fitness monitoring device 50 records real-time fitness data for the user as the user travels on the selected off-road trail, and this real-time fitness data is transmitted to the navigation device 20.

Step 112: The navigation device 20 synchronizes the real-time fitness data, the recorded video, and the recorded latitude and longitude coordinates and elevation data generated as a result of the user traveling on the selected off-road trail.

Step 114: The synchronized trail data is stored in the server 16 to generate a newly created overview of the selected off-road trail, and the process ends.

Step 116: The user reviews the overview of the selected off-road trail to see a video preview of the selected off-road trail and to see an indication of recommended minimum health guidelines for the selected off-road trail. The recommended minimum health guidelines can either be overall recommended minimum health guidelines for the entire selected off-road trail, or can be recommended minimum health guidelines for individual segments of the selected off-road trail.

Step 118: Determine if the user's health condition qualifies the user for the selected off-road trail. When analyzing the user's health condition, both the user's real-time fitness data and the user's historical fitness data can be considered. If the user's health condition indicates that the user is qualified for the selected off-road trail, go to step 120. If the user's health condition indicates that the user is not qualified for the selected off-road trail, go to step 126.

Step 120: The user may proceed with the selected off-road trail since the user's health condition qualifies the user for the selected off-road trail.

Step 122: Determine if the user has stopped traveling on the selected off-road trail. Stopping may indicate either that the user has had a physical or mental problem while traveling on the selected off-road trail, or that the user's vehicle (if applicable) has broken down. If the user has stopped traveling while on the selected off-road trail, go back to step 116. This will give the user the chance to review the overview of the selected off-road trail to decide if the user would like to proceed or to change plans. Otherwise, if the user has not stopped traveling while on the selected off-road trail, proceed to step 124.

Step 124: Determine whether the user has reached the end of the selected off-road trail. If so, the process ends. If not, go back to step 120.

Step 126: The navigation device 20 will calculate an alternate route since the user is not qualified for travelling on the selected off-road trail.

Step 128: Determine if the user's health condition qualifies the user for the alternate route. When analyzing the user's health condition, both the user's real-time fitness data and the user's historical fitness data can be considered. If the user's health condition indicates that the user is qualified for the alternate route, go to step 130. If the user's health condition indicates that the user is not qualified for the alternate route, go back to step 126 to calculate another alternate route.

Step 130: Determine if the user has reached the end of the alternate route. If so, the process ends. If not, go back to step 128.

In summary, the present invention allows users to see which off-road trails are suitable or not suitable for the user based on the associated recommended minimum health guidelines associated with a selected off-road trail or even based on the elevation or elevation changes of the selected off-road trail. The present invention can also monitor the user's real-time fitness data and the user's historical fitness data to determine if the user is qualified to embark on or continue on the selected off-road trail. The user is also given the opportunity to see an overview of the selected off-road trail so that the user can easily and conveniently find out more details about the selected off-road trail, including the recommended minimum health guidelines. The overview can be seen before the user travels to the selected off-road trail or while the user is already on the selected off-road trail. Moreover, in the event that the user needs assistance with leaving the selected off-road trail that the user is currently traveling on, an alternate route can be presented to the user for helping to safely guide the user away from the selected off-road trail.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A method of previewing off-road trails and viewing associated health requirements, the method comprising:
a navigation device receiving selection of an off-road trail from a user; and
the navigation device displaying an overview of the selected off-road trail in response to receiving selection of the selected off-road trail from the user, the overview of the selected off-road trail indicating latitude and longitude coordinates associated with the selected off-road trail, elevation data associated with the selected off-road trail, and recommended minimum health guidelines that indicate what kind of fitness statistics the user is recommended to have in order for the user to attempt the selected off-road trail.

2. The method of claim 1, further comprising:
receiving real-time fitness data from a fitness monitoring device worn by the user, the fitness monitoring device containing at least one sensor for sensing the real-time fitness data over time;
recording the real-time fitness data for the user as the user travels on the selected off-road trail;
recording video with a camera of a navigation device as the user travels on the selected off-road trail;
recording latitude and longitude coordinates and elevation data with the navigation device as the user travels on the selected off-road trail; and
synchronizing, with the navigation device, the real-time fitness data, the recorded video, and the recorded latitude and longitude coordinates and elevation data generated as a result of the user traveling on the selected off-road trail to produce synchronized trail data.

3. The method of claim 2, further comprising:
storing the synchronized trail data in an online server; and
updating the overview of the selected off-road trail using the stored synchronized trail data.

4. The method of claim 2, further comprising:
monitoring the user's real-time fitness data while the user travels on the selected off-road trail;
generating with the navigation device an alternate route for the user to follow instead of the selected off-road trail in response to determining that the user's real-time fitness data indicates that the user is not qualified to travel on the selected off-road trail; and
providing navigational assistance to the user for guiding the user to follow the alternate route.

5. The method of claim 2, further comprising issuing a warning if the user's current speed is higher than recommended for the user based on the user's real-time fitness data while the user travels on the selected off-road trail.

6. The method of claim 1, further comprising allowing the user to review the overview of the selected off-road trail while the user travels on the selected off-road trail.

7. The method of claim 1, wherein displaying the overview of the selected off-road trail comprises showing a video of the selected off-road trail, the overview of the selected off-road trail displaying latitude and longitude coordinates associated with segments of the selected off-road trail, elevation data associated with segments of the selected off-road trail, and recommended minimum health guidelines associated with segments of the selected off-road trail while the video is playing.

8. The method of claim 1, further comprising:
storing the user's historical fitness data in advance;
comparing the user's historical fitness data to the recommended minimum health guidelines associated with the selected off-road trail;
determining if the user is qualified to travel on the selected off-road trail according to the comparison of the user's historical fitness data to the recommended minimum health guidelines associated with the selected off-road trail; and
permitting the user to travel on the selected off-road trail when the user's historical fitness data conforms to the recommended minimum health guidelines associated with the selected off-road trail.

9. The method of claim 1, wherein the overview of the selected off-road trail is viewable for individual segments of the selected off-road trail.

10. The method of claim 1, wherein the navigation device is a personal navigation device or a mobile phone, and the fitness monitoring device is a fitness band.

11. A system for previewing off-road trails and viewing associated health requirements, the system comprising:
a navigation device, comprising:
a user interface receiving selection of an off-road trail from a user, and displaying an overview of the selected off-road trail in response to receiving selection of the selected off-road trail from the user, the overview of the selected off-road trail indicating latitude and longitude coordinates associated with the selected off-road trail, elevation data associated with the selected off-road trail, and recommended minimum health guidelines that indicate what kind of fitness statistics the user is recommended to have in order for the user to attempt the selected off-road trail.

12. The system of claim 11, further comprising:
a fitness monitoring device worn by the user, the fitness monitoring device comprising:
at least one sensor sensing real-time fitness data over time; and
a memory recording the real-time fitness data for the user as the user travels on the selected off-road trail;
a first wireless transceiver wirelessly communicating with the navigation device; and
the navigation device further comprises:
a camera recording video of as the user travels on the selected off-road trail;
a Global Positioning System (GPS) receiver recording latitude and longitude coordinates and elevation data as the user travels on the selected off-road trail;
a second wireless transceiver wirelessly communicating with the first wireless transceiver of the fitness monitoring device; and
a processor synchronizing the real-time fitness data, the recorded video, and the recorded latitude and longitude coordinates and elevation data generated as a result of the user traveling on the selected off-road trail to produce synchronized trail data.

13. The system of claim 12, further comprising:
an online server storing the synchronized trail data received from the navigation device, the online server updating the overview of the selected off-road trail using the stored synchronized trail data.

14. The system of claim 12, wherein the fitness monitoring device monitors the user's real-time fitness data while the user travels on the selected off-road trail, and the navigation device further comprises routing software executed by the processor, the routing software generating an alternate route for the user to follow instead of the selected off-road trail in response to the processor determining that the user's real-time fitness data indicates that the user is not qualified to travel on the selected off-road trail, the routing software providing navigational assistance to the user for guiding the user to follow the alternate route.

15. The system of claim 12, wherein the user interface of the navigation device issues a warning if the user's current speed is higher than recommended for the user based on the user's real-time fitness data while the user travels on the selected off-road trail.

16. The system of claim 11, wherein the user interface of the navigation device permits the user to review the overview of the selected off-road trail while the user travels on the selected off-road trail.

17. The system of claim 11, wherein the user interface of the navigation device shows showing a video of the selected off-road trail, the overview of the selected off-road trail displaying latitude and longitude coordinates associated with segments of the selected off-road trail, elevation data associated with segments of the selected off-road trail, and recommended minimum health guidelines associated with segments of the selected off-road trail while the video is playing.

18. The system of claim 11, wherein the processor compares the user's stored historical fitness data to the recommended minimum health guidelines associated with the selected off-road trail and determines if the user is qualified to travel on the selected off-road trail according to the comparison of the user's historical fitness data to the recommended minimum health guidelines associated with the selected off-road trail, wherein the user interface permits the user to travel on the selected off-road trail when the user's historical fitness data conforms to the recommended minimum health guidelines associated with the selected off-road trail.

19. The system of claim 11, wherein the overview of the selected off-road trail is viewable for individual segments of the selected off-road trail.

20. The system of claim 11, wherein the navigation device is a personal navigation device or a mobile phone, and the fitness monitoring device is a fitness band.

* * * * *